(12) United States Patent
Allen et al.

(10) Patent No.: US 7,339,075 B2
(45) Date of Patent: Mar. 4, 2008

(54) LIGAND SYNTHESIS

(75) Inventors: Nathan Tait Allen, Norristown, PA (US); Brian Leslie Goodall, Ambler, PA (US); Thomas Cleveland Kirk, Ivyland, PA (US); Lester Howard McIntosh, III, Green Lane, PA (US)

(73) Assignee: Rohm and Haas Company, Philadelphia, PA (US)

( * ) Notice: Subject to any disclaimer, the term of this patent is extended or adjusted under 35 U.S.C. 154(b) by 38 days.

(21) Appl. No.: 11/457,996

(22) Filed: Jul. 17, 2006

(65) Prior Publication Data

US 2007/0287847 A1    Dec. 13, 2007

Related U.S. Application Data

(60) Provisional application No. 60/713,172, filed on Aug. 31, 2005.

(51) Int. Cl.
*C07F 5/02* (2006.01)
(52) U.S. Cl. ............................................. 562/35; 568/8
(58) Field of Classification Search ................. 562/35; 568/8
See application file for complete search history.

(56) References Cited

U.S. PATENT DOCUMENTS

| 4,689,437 A | | 8/1987 | Murray |
| 5,760,286 A | * | 6/1998 | Brandvold .................... 562/35 |
| 6,060,569 A | | 5/2000 | Bennett et al. |

FOREIGN PATENT DOCUMENTS

| EP | 0 589 527 | 7/1999 |
| WO | WO 00/02890 A | 1/2000 |
| WO | WO 0006615 | 2/2000 |

OTHER PUBLICATIONS

Hearley, et al., New Single-Site Palladium Catalysis for the Nonalternative Copolymerization of Ethylene and Carbon Monoxide, ORGANOMETALLICS, vol. 24, pp. 2755-2763 (2005).
Drent, et al., Palladium catalysed copolymerization of ethene with alkylacrylates: polar commonomer built into the linear polymer chain, Chem. Commun. pp. 744-745 (2002).
Schultz, et al., Palladium(II) Complexes with Chelating P,O-Ligands as Catalysts for the Heck Reaction, SYNTHESIS No. 6, pp. 1005-1011 (2005).
Katho, et al., Formation and Solid State Structures of Highly Crystalline Guanidinium Salts of Sulfonated Tertiary Phosphanes, Adv. Synth. Catal. No. 3/4, pp. 278-282 (2002).
Genet, et al., Recent developments of palladium(O) catalyzed reactions in aqueous medium, J. Organometallic Chemistry, vol. 576, Issues 1 2, pp. 305-317 (1999).
Kaye, et al., The Use of Catalytic Amounts of CuCl and Other Improvements in the Benzyne Route to Biphenyl-Based Phosphine Ligands, Adv. Synth. Catal. No. 8, pp. 789-794 (2001.

* cited by examiner

*Primary Examiner*—Yvonne Eyler
*Assistant Examiner*—Yate' K Cutliff
(74) *Attorney, Agent, or Firm*—Thomas S. Deibert

(57) ABSTRACT

Ligand synthesis methods for the preparation of ligands having the formula

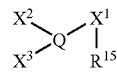

wherein Q is selected from phosphorus, arsenic and antimony; wherein $X^1$, $X^2$ and $X^3$ are carbon anions; and, wherein $R^{15}$ is selected from $-SO_3$, $-SO_2N(R^{18})$, $-CO_2$, $-PO_3$, $-AsO_3$, $-SiO_2$, $-C(CF_3)_2O$; where $R^{18}$ is selected from a hydrogen, a halogen, a hydrocarbyl group and a substituted hydrocarbyl group, are disclosed. Also disclosed are methods of complexing the ligands with late transition metals to form catalyst complexes that catalyze polymerization reactions and/or Heck coupling reactions.

7 Claims, No Drawings

LIGAND SYNTHESIS

This Application claims the benefit of U.S. Provisional Patent Application No. 60/713,172, filed on Aug. 31, 2005.

This invention was made with United States Government support under ATP Award No. 70NANB4H3014 awarded by the National Institute of Standards and Technology (NIST). The United States Government has certain rights in the invention.

The present invention relates to a method of synthesizing ligand structures that may be complexed with a late transition metal to form catalyst complexes useful in facilitating various polymerization reactions and/or Heck coupling reactions.

The identification of new ligands for late transition metals and of commercially viable methods for making such ligands are important. For example, the identification of new ligands that complex with late transition metals to form catalyst complexes that are active for catalyzing polymerization reactions is of particular importance. That is, there remains an industry wide need for new molecular catalyst complexes that are capable of polymerizing polar monomers in a controlled fashion and for copolymerizing polar monomers with olefins (e.g., ethylene, propylene) under mild reaction conditions. Of the many approaches to modifying the properties of a polymer, the incorporation of functional groups into an otherwise non-polar material would be ideal in many situations. The incorporation of polar groups into a non-polar material can result in modification to various physical properties of the resultant copolymer, for example, toughness, adhesion, barrier properties and surface properties. Changes in these physical properties can result in improved solvent resistance, miscibility with other polymers and rheological properties, and product performance such as paintability, dyeability, printability, gloss, hardness and mar resistance.

The identification of new ligands that complex with late transition metals to form catalyst complexes that are active for Heck coupling reactions is also or particular commercial importance.

One approach to the preparation of ligands is disclosed in U.S. Pat. No. 5,760,286 to Brandvold. Brandvold disclose a method for the preparation of ligands according to the formula IV

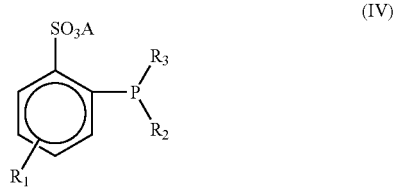

where A is selected from hydrogen, alkali earth metal, alkaline earth metal, quaternary ammonium, and a phosphonium group; $R_1$ is selected from the group consisting of hydrogen, an alkyl group having from 1 up to about 20 carbon atoms, an aromatic group or an aralkyl group; $R_2$ is selected from the group consisting of an alkyl group of from 1 up to about 20 carbon atoms, an aromatic group or fused aromatic group, an aralkyl group, and a cycloalkyl group having from 5 up to about 10 ring carbon atoms; and, $R_3$ is selected from the group consisting of hydrogen, an alkyl group of from 1 up to about 20 carbon atoms, an aromatic group or an aralkyl group, and a cycloalkyl group having from 5 up to about 10 ring carbon atoms, comprising: a first reaction of compounds of formula II,

with compounds of formula I

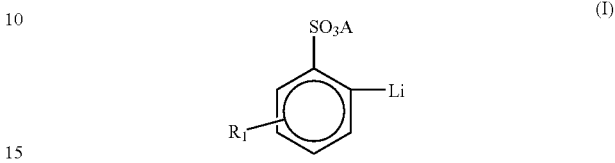

to afford products of formula III

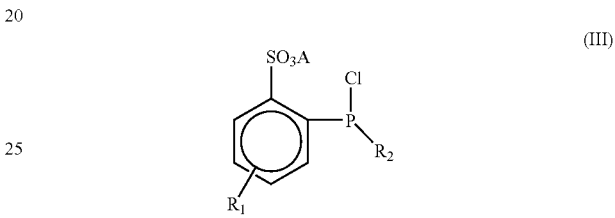

where said first reaction proceeds by addition of a heterogeneous mixture of one molar proportion of the compound of formula I dispersed in an organic phase to a solution of the compound of formula II in an organic phase to afford a reaction mixture, said addition carried out at a rate such that the reaction mixture is at all times homogeneous, and; subsequent alkylation of the compound of formula III by an organometallic compound of formula $R_3M$ to yield the ligand of formula IV where $R_3M$ is a Grignard reagent or an organolithium.

Nevertheless, there remains a need for new ligands and new ligand synthesis methods that provide such ligands in good yield and in relatively high purity.

In one aspect of the present invention, there is provided a process for making a ligand having the formula

wherein the process comprises the following reactions:

| | | | |
|---|---|---|---|
| (a) | $X^1(R^{15})$-$E^1$ + $V^1$-$Q(V^3)V^2$ | → | $X^1(R^{15})$-$Q(V^3)V^2$ (Compound I) |
| (b) | $X^2$-$E^2$ + $X^1(R^{15})$-$Q(V^3)V^2$ (Compound I) | → | $X^1(R^{15})$-$Q(V^3)$-$X^2$ (Compound II) |
| (c) | $X^3$-$E^3$ + $X^1(R^{15})$-$Q(V^3)$-$X^2$ (Compound II) | → | $X^1(R^{15})$-$Q(X^3)$-$X^2$ (Compound III); | wherein Q is selected from phosphorus, arsenic and antimony; wherein $E^1$, $E^2$ and $E^3$ are electrophilic metals; wherein $V^1$, $V^2$ and $V^3$ are weakly-basic anions; wherein $X^1$, $X^2$ and $X^3$ are carbon anions; and, wherein $R^{15}$ is selected from —$SO_3$, —$SO_2N(R^{18})$, —$CO_2$, —$PO_3$, —$AsO_3$, —SiO$_2$, —C(CF$_3$)$_2$O; where R$^{18}$ is selected from a hydrogen, a halogen, a hydrocarbyl group and a substituted hydrocarbyl group.

In another aspect of the present invention, there is provided a process for making a ligand having the formula

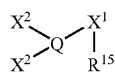

wherein the process comprises the following reactions:

| | | | |
|---|---|---|---|
| (i) | X$^1$(R$^{15}$)-E$^1$ + V$^1$-Q(V$^3$)V$^2$ | → | X$^1$(R$^{15}$)-Q(V$^3$)V$^2$ (Compound I) |
| (ii) | 2 X$^2$-E$^2$ + X$^1$(R$^{15}$)-Q(V$^3$)V$^2$ (Compound I) | → | X$^1$(R$^{15}$)-Q(X$^2$)X$^2$ (Compound IV); | wherein Q is selected from phosphorus, arsenic and antimony; wherein E$^1$ and E$^2$ are electrophilic metals; wherein V$^1$, V$^2$ and V$^3$ are weakly-basic anions; wherein X$^1$ and X$^2$ are carbon anions; and, wherein R$^{15}$ is selected from —SO$_3$, —SO$_2$N(R$^{18}$), —CO$_2$, —PO$_3$, —AsO$_3$, —SiO$_2$, —C(CF$_3$)$_2$O; where R$^{18}$ is selected from a hydrogen, a halogen, a hydrocarbyl group and a substituted hydrocarbyl group.

The term "protecting group" as used herein and in the appended claims refers to a group of atoms that when attached to a reactive group in a molecule masks, reduces or prevents undesired reactions with the reactive group. The use of protecting groups is well known in the art. Examples of protecting groups and of how they may be used can be found, among other places, in *Protecting Groups in Organic Chemistry*, J. W. F. McOmie, (ed.), 1973, Plenum Press and *Protective Groups In Organic Synthesis*, (Wiley, John & Sons, Inc. 3$^{rd}$ ed. 1999).

In some embodiments of the present invention, the process for making a ligand having the formula

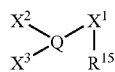

comprises the following reactions:

| | | | |
|---|---|---|---|
| (a) | X$^1$(R$^{15}$)-E$^1$ + V$^1$-Q(V$^3$)V$^2$ | → | X$^1$(R$^{15}$)-Q(V$^3$)V$^2$ (Compound I) |
| (b) | X$^2$-E$^2$ + X$^1$(R$^{15}$)-Q(V$^3$)V$^2$ (Compound I) | → | X$^1$(R$^{15}$)-Q(V$^3$)-X$^2$ (Compound II) |
| (c) | X$^3$-E$^3$ + X$^1$(R$^{15}$)-Q(V$^3$)-X$^2$ (Compound II) | → | X$^1$(R$^{15}$)-Q(X$^3$)-X$^2$ (Compound III); | wherein Q is selected from phosphorus, arsenic and antimony; alternatively Q is selected from phosphorus and arsenic; alternatively Q is phosphorus;

wherein E$^1$, E$^2$ and E$^3$ are independently selected from lithium, magnesium, potassium, beryllium, sodium, scandium, yttrium, titanium, lanthanum, cerium, praseodymium, neodymium, samarium, europium, gadolinium, terbium, dysprosium, holmium, erbium, thulium, ytterbium and lutetium; alternatively E$^1$, E$^2$ and E$^3$ are independently selected from lithium, magnesium, potassium and sodium; alternatively E$^1$, E$^2$ and E$^3$ are lithium;

wherein V$^1$, V$^2$ and V$^3$ are independently selected from chloride, bromide, fluoride, iodide, toluenesulfonate, methansulfonate, trifluoromethansulfonate, benzenesulfonate; alternatively V$^1$, V$^2$ and V$^3$ are chloride;

wherein X$^1$, X$^2$ and X$^3$ are carbon anions; and, wherein R$^{15}$ is selected from —SO$_3$, —SO$_2$N(R$^{18}$), —CO$_2$, —PO$_3$, —AsO$_3$, —SiO$_2$, —C(CF$_3$)$_2$O; alternatively R$^{15}$ is selected from —SO$_3$ and —SO$_2$N(R$^{18}$); alternatively R$^{15}$ is —SO$_3$; where R$^{18}$ is selected from a hydrogen, a halogen, a hydrocarbyl group and a substituted hydrocarbyl group; alternatively R$^{18}$ is selected from a hydrogen; a halogen; and, a substituted or unsubstituted substituent selected from C$_1$-C$_{20}$ alkyl, C$_3$-C$_{20}$ cycloalkyl, C$_2$-C$_{20}$ alkenyl, C$_2$-C$_{20}$ alkynyl, aryl, arylalkyl, alkylaryl, phenyl, biphenyl, C$_1$-C$_{20}$ carboxylate, C$_1$-C$_{20}$ alkoxy, C$_2$-C$_{20}$ alkenyloxy, C$_2$-C$_{20}$ alkynyloxy, aryloxy, C$_2$-C$_{20}$ alkoxycarbonyl, C$_1$-C$_{20}$ alkylthio, C$_1$-C$_{20}$ alkylsulfonyl, C$_1$-C$_{20}$ alkylsulfinyl, and silyl.

In some aspects of these embodiments, X$^1$, X$^2$ and X$^3$ are all different. In some aspects of these embodiments, X$^2$ and X$^3$ are the same.

In some embodiments of the present invention, reactions (a), (b) and (c) are performed sequentially in the same vessel.

In some embodiments of the present invention, the reaction temperature during reaction (a) is lower than the reaction temperature during reaction (b) and wherein the reaction temperature during reaction (b) is lower than the reaction temperature during reaction (c).

In some embodiments of the present invention, reaction (b) proceeds in the same vessel as reaction (a) without isolation of Compound I.

In some embodiments of the present invention, reaction (c) proceeds in the same vessel as reaction (b) without isolation of Compound II.

In some embodiments of the present invention, the process for making a ligand having the formula

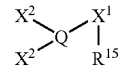

comprises the following reactions:

| | | | |
|---|---|---|---|
| (i) | X$^1$(R$^{15}$)-E$^1$ + V$^1$-Q(V$^3$)V$^2$ | → | X$^1$(R$^{15}$)-Q(V$^3$)V$^2$ (Compound I) |
| (ii) | 2 X$^2$-E$^2$ + X$^1$(R$^{15}$)-Q(V$^3$)V$^2$ (Compound I) | → | X$^1$(R$^{15}$)-Q(X$^2$)-X$^2$ (Compound IV); | wherein Q is selected from phosphorus, arsenic and antimony; alternatively Q is selected from phosphorus and arsenic; alternatively Q is phosphorus;

wherein E$^1$ and E$^2$ are independently from lithium, magnesium, potassium, beryllium, sodium, scandium, yttrium, titanium, lanthanum, cerium, praseodymium, neodymium, samarium, europium, gadolinium, terbium, dysprosium, holmium, erbium, thulium, ytterbium and lutetium; alternatively E$^1$ and E$^2$ are independently selected from lithium, magnesium, potassium and sodium; alternatively E$^1$ and E$^2$ are lithium;

wherein V¹, V² and V³ are independently selected from chloride, bromide, fluoride, iodide, toluenesulfonate, methansulfonate, trifluoromethansulfonate, benzenesulfonate; alternatively V¹, V² and V³ are chloride;

wherein X¹ and X² are carbon anions;

wherein $R^{15}$ is selected from —$SO_3$, —$SO_2N(R^{18})$, —$CO_2$, —$PO_3$, —$AsO_3$, —$SiO_2$, —$C(CF_3)_2O$; alternatively $R^{15}$ may be selected from —$SO_3$ and —$SO_2N(R^{18})$; alternatively $R^{15}$ is —$SO_3$; where $R^{18}$ is selected from a hydrogen, a halogen, a hydrocarbyl group and a substituted hydrocarbyl group; alternatively where $R^{18}$ is selected from a hydrogen; a halogen; and, a substituted or unsubstituted substituent selected from $C_1$-$C_{20}$ alkyl, $C_3$-$C_{20}$ cycloalkyl, $C_2$-$C_{20}$ alkenyl, $C_2$-$C_{20}$ alkynyl, aryl, arylalkyl, alkylaryl, phenyl, biphenyl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl, $C_1$-$C_{20}$ alkylsulfinyl, and silyl.

In some embodiments of the present invention, reactions (i) and (ii) are performed sequentially in the same vessel.

In some embodiments of the present invention, the reaction temperature during reaction (i) is lower than the reaction temperature during reaction (ii).

In some embodiments of the present invention, reaction (ii) proceeds in the same vessel as reaction (i) without isolation of Compound I.

In some embodiments of the present invention, $X^1$, $X^2$ and $X^3$ are independently selected from aliphatic hydrocarbyl groups and aromatic hydrocarbyl groups; alternatively $X^1$, $X^2$ and $X^3$ are independently selected from aliphatic hydrocarbyl groups and aromatic hydrocarbyl groups having up to 30 carbon atoms; alternatively $X^1$, $X^2$ and $X^3$ are independently selected from alkyl, cycloalkyl, alkenyl, alkynyl, aryl, arylalkyl, alkylaryl, phenyl, biphenyl, carboxylate, alkoxy, alkenyloxy, alkynyloxy, aryloxy, alkoxycarbonyl, alkylthio, alkylsulfonyl, alkylsulfinyl, silyl, and derivatives thereof; alternatively $X^1$, $X^2$ and $X^3$ are independently selected from $C_1$-$C_{20}$ alkyl, $C_3$-$C_{20}$ cycloalkyl, $C_2$-$C_{20}$ alkenyl, $C_2$-$C_{20}$ alkynyl, aryl, arylalkyl, alkylaryl, phenyl, biphenyl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl, $C_1$-$C_{20}$ alkylsulfinyl, silyl, and derivatives thereof; alternatively $X^1$, $X^2$ and $X^3$ are substituted aryl groups. In some aspects of these embodiments, $X^2$ and $X^3$ are independently selected from ortho substituted aryl groups; alternatively $X^2$ and $X^3$ are independently selected from aryl groups with an ortho substituted phenyl; alternatively $X^2$ and $X^3$ are independently selected from aryl groups with an ortho substituted, substituted phenyl; alternatively $X^2$ and $X^3$ are independently selected from aryl groups with an ortho substituted, substituted phenyl having a formula 2,6-$R^{16}R^{17}$-phenyl; where $R^{16}$ and $R^{17}$ are independently selected from $C_1$-$C_{20}$ alkyl, $C_3$-$C_{20}$ cycloalkyl, $C_2$-$C_{20}$ alkenyl, $C_2$-$C_{20}$ alkynyl, aryl, arylalkyl, alkylaryl, phenyl, biphenyl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl, $C_1$-$C_{20}$ alkylsulfinyl, silyl, and derivatives thereof, alternatively $X^2$ and $X^3$ are aryl groups with an ortho substituted 2,6-dimethoxy phenyl.

In some embodiments of the present invention, $X^1(R^{15})$—$E^1$, $X^2$—$E^2$ and $X^3$—$E^3$ are according to formulas I, II, and III, respectively,

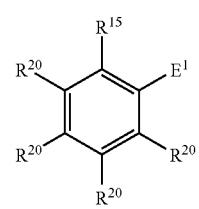

(I)

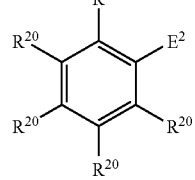

(II)

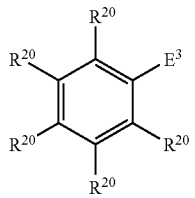

(III)

wherein $E^1$, $E^2$ and $E^3$ are independently selected from lithium, magnesium, potassium, beryllium, sodium, scandium, yttrium, titanium, lanthanum, cerium, praseodymium, neodymium, samarium, europium, gadolinium, terbium, dysprosium, holmium, erbium, thulium, ytterbium and lutetium; alternatively $E^1$, $E^2$ and $E^3$ are independently selected from lithium, magnesium, potassium and sodium; alternatively $E^1$, $E^2$ and $E^3$ are lithium;

wherein $R^{15}$ is selected from —$SO_3$, —$SO_2N(R^{18})$, —$CO_2$, —$PO_3$, —$AsO_3$, —$SiO_2$, —$C(CF_3)_2O$; alternatively $R^{15}$ is selected from —$SO_3$ and —$SO_2N(R^{18})$; alternatively $R^{15}$ is —$SO_3$; where $R^{18}$ is selected from a hydrogen, a halogen, a hydrocarbyl group and a substituted hydrocarbyl group; alternatively $R_{18}$ is selected from a hydrogen, a halogen, and a substituted or unsubstituted substituent selected from $C_1$-$C_{20}$ alkyl, $C_3$-$C_{20}$ cycloalkyl, $C_2$-$C_{20}$ alkenyl, $C_2$-$C_{20}$ alkynyl, aryl, arylalkyl, alkylaryl, phenyl, biphenyl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl, $C_1$-$C_{20}$ alkylsulfinyl, and silyl; and, wherein each $R^{20}$ is independently selected from a hydrogen, a halogen, and a substituted or unsubstituted substituent selected from $C_1$-$C_{20}$ alkyl, $C_3$-$C_{20}$ cycloalkyl, $C_2$-$C_{20}$ alkenyl, $C_2$-$C_{20}$ alkynyl, aryl, arylalkyl, alkylaryl, phenyl, biphenyl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl, $C_1$-$C_{20}$ alkylsulfinyl, and silyl; alternatively wherein each $R^{20}$ is independently selected from a hydrogen, a phenyl and a substituted phenyl; alternatively wherein each $R^{20}$ is independently selected from a hydrogen and a substituted phenyl; alternatively wherein each $R^{20}$ is independently selected from a hydrogen and an ortho substituted phenyl. In some aspects of these embodiments, the substituted phenyl is an ortho substituted phenyl. In some aspects of these embodiments, the ortho substituted phenyl is 2,6—$R^{16}R^{17}$-phenyl; where $R^{16}$ and $R^{17}$ are selected from $C_1$-$C_{20}$ alkyl, $C_3$-$C_{20}$ cycloalkyl, $C_2$-$C_{20}$ alkenyl, $C_2$-$C_{20}$ alkynyl, aryl, arylalkyl, alkylaryl, phenyl, biphenyl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl, $C_1$-$C_{20}$ alkylsulfinyl, and silyl. In some aspects of these embodiments, the ortho substituted phenyl is 2,6-dimethoxy phenyl.

In some embodiments of the present invention, each $R^{20}$ on formula II is independently selected from a hydrogen, a phenyl and a substituted phenyl. In some aspects of these embodiments, both $R^{20}$'s on formula II that are ortho to $E^2$ are selected from a phenyl and a substituted phenyl; alternatively a substituted phenyl. In some aspects of these embodiments, one $R^{20}$ that is ortho to $E^2$ and the $R^{20}$ that is para to $E^2$ are selected from a phenyl and a substituted phenyl; alternatively a substituted phenyl. In some aspects of these embodiments, both $R^{20}$'s on formula II that are ortho to $E^2$ and the $R^{20}$ that is para to $E^2$ are selected from a phenyl and a substituted phenyl; alternatively a substituted phenyl. In some aspects of these embodiments, the substituted phenyl is 2,6-dimethoxy phenyl.

In some embodiments of the present invention, each $R^{20}$ on formula III is independently selected from a hydrogen, a phenyl and a substituted phenyl. In some aspects of these embodiments, both $R^{20}$'s on formula III that are ortho to $E^3$ are selected from a phenyl and a substituted phenyl; alternatively a substituted phenyl. In some aspects of these embodiments, one $R^{20}$ that is ortho to $E^3$ and the $R^{20}$ that is para to $E^3$ are selected from a phenyl and a substituted phenyl; alternatively a substituted phenyl. In some aspects of these embodiments, both $R^{20}$'s on formula II that are ortho to $E^3$ and the $R^{20}$ that is para to $E^3$ are selected from a phenyl and a substituted phenyl; alternatively a substituted phenyl. In some aspects of these embodiments, the substituted phenyl is 2,6-dimethoxy phenyl.

In some embodiments of the present invention, the ligand having formula

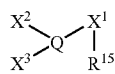

is selected from Structures I-XV presented in Table 1. In some aspects of these embodiments, the ligand is selected from Structures I, XI, and XIV. In some aspects of these embodiments, the ligand is selected from Structures I and XIV. In some aspects of these embodiments, the ligand is Structure I. In some aspects of these embodiments, the ligand is Structure XIV.

In some embodiments of the present invention, the reaction conditions for reaction (a) or reaction (i) are controlled such that the temperature of the reagents are maintained at a temperature which enables the reaction of $V^1$—$Q(V^3)V^2$ with $X^1(R^{15})$—$E^1$ to proceed while inhibiting the reaction of $V^1$—$Q(V^3)V^2$ with Compound I. In some aspects of these embodiments, the reaction temperature for reaction (a) or reaction (i) is maintained at $\leq 40°$ C.; alternatively $\leq 0°$ C.; alternatively $\leq -20°$ C.; alternatively $\leq -50°$ C.; alternatively $-90$ to $-70°$ C.

In some embodiments of the present invention, the $X^1(R^{15})$—$E^1$ is slowly added into a solution of $V^1$—$Q(V^3)$ $V^2$ with sufficient agitation such that the concentration of $V^1$—$Q(V^3)V^2$ is maintained in excess relative to $X^1(R^{15})$— $E^1$ such that even localized excesses of $X^1(R^{15})$—$E^1$ relative to $V^1$—$Q(V^3)V^2$ are avoided. By maintaining $V^1$—$Q(V^3)V^2$ in excess relative to $X^1(R^{15})$—$E^1$, the reaction of $X^1(R^{15})$— $E^1$ with $V^1$—$Q(V^3)V^2$ may be favored over the reaction of $X^1(R^{15})$—$E^1$ with Compound I.

In some embodiments of the present invention, the reaction conditions for reaction (b) are controlled such that the temperature of the reagents are maintained at a temperature which enables the reaction of Compound I with $X^2$—$E^2$ to proceed while inhibiting the reaction of Compound I with Compound II. In some aspects of these embodiments, the reaction temperature during reaction (b) is maintained at $\leq 25°$ C.; alternatively $\leq 0°$ C.; alternatively $\leq -30°$ C.; alternatively $\leq -70°$ C.

In some embodiments of the present invention, the process for making the ligand is performed in a substantially oxygen-free atmosphere. In some aspects of these embodiments, the process is performed in a nitrogen atmosphere. In some aspects of these embodiments, the process is performed in an argon atmosphere.

In some embodiments of the present invention, no protecting groups are used in the process to prepare the ligands.

The ligands prepared by the synthesis methods of the present invention may be complexed with a late transition metal, such as palladium and nickel, to form late transition metal catalyst complexes that may be used for example as polymerization catalysts and/or as Heck coupling reaction catalysts.

Some embodiments of the present invention will now be described in detail in the following Examples. All fractions and percentages set forth below in the Examples are by weight unless otherwise specified. The chemical structures presented in Table 1 have been drawn according to the general rules for drawing Lewis structures of molecules as described in, for example, Brown, et al., *Organic Chemistry*, Brooks-Cole, 4th ed 2004.

EXAMPLES 1-16

Ligand Synthesis

Following the general procedure presented below using Component A and Component B identified in Table 1 in the amounts listed in Table 1, the Product Solids listed in Table 1 were prepared with the reported yield for examples 1-15, respectively.

Component A was added to a 100 mL flask ("Flask A") then placed under vacuum and refilled with nitrogen and charged with 60 mL of tetrahydrofuran (THF). Flask A was then placed in an ice bath and allowed to cool to 0° C. 10.1 mL of 2.5 molar n-BuLi was then injected. Flask A was then placed in a dry ice/acetone bath and allowed to cool to about −78° C.

A separate 500 mL Schlenk flask ("Flask B") was placed under vacuum. Flask B was purged with nitrogen and charged with ~50 mL of THF. Flask B was then placed in a dry ice/acetone bath and allowed to cool to about −78° C. 1.10 mL of $PCl_3$ was then added to Flask B with agitation. The contents of Flask A were then slowly transferred to Flask B using a cannula with vigorous agitation.

A separate 100 mL flask ("Flask C") was purged and filled with nitrogen. Flask C was then charged with ~60 mL of THF and Component B. Flask C was then placed in a dry ice/acetone bath and allowed to cool with agitation to about −78° C. 10.1 mL of 2.5 molar n-BuLi was added to Flask C and allowed to react for about 15 minutes. The contents of Flask C were then transferred to Flask B, maintained at −78° C., using a cannula with continued vigorous agitation.

Following the complete addition of the contents of Flask C into Flask B, Flask B was allowed to warm to room temperature for about 30 minutes. The contents of Flask B were then poured into a 500 mL recovery flask (Flask D) and the THF was removed, leaving a solid. The solid in Flask D was then mixed with distilled water and then transferred to a separation flask (Flask E). 100 mL of $CH_2Cl_2$ was added to the contents of Flask E. Flask E was shaken to mix the two layers. About 5 mL of concentrated HCl was then added to Flask E. Flask E was shaken again. The mixture in Flask E was then allowed to settle, forming two layers—an organic phase on the bottom and a aqueous phase on the top. The organic layer was collected. The aqueous phase was washed with 50 mL of $CH_2Cl_2$. The organic wash material was collected and added to the previously collected organic layer material. The combined organic material was then contacted with $MgSO_4$ and rotovaped to dryness, leaving a solid. The solid was then washed first with diethyl ether and then with THF to remove impurities. The washed Product Solid was collected by filtration with the yield reported in Table 1.

TABLE 1

| | | | Product Solid/Yield | |
|---|---|---|---|---|
| Ex# | Component A | Component B | Chemical Name | Structure |
| 1 | benzene sulfonic acid (2.10 g) | 2',6'dimethoxy-2-biphenylbromide (7.45 g) | 2-(bis-(2',6'dimethoxy-2-biphenyl)-phosphino) benzene sulfonic acid (~5 g) | Structure I |
| 2 | benzene sulfonic acid (2.10 g) | 2-bromoethylbenzene (4.7 g) | 2-(bis-(2-ethylphenyl)-phosphino) benzene sulfonic acid (~2 g) | Structure II |
| 3 | benzene sulfonic acid (2.10 g) | 4-bromo-N,N-dimethylaniline (5.1 g) | 2-(bis(4-dimethylaminophenyl)-phosphino benzene sulfonic acid (~2 g) | Structure III |

TABLE 1-continued

| Ex# | Component A | Component B | Product Solid/Yield | |
|---|---|---|---|---|
| | | | Chemical Name | Structure |
| 4 | napthalenesulfonic acid (2.63 g) | 2-bromoanisole (4.75 g) | 2-(bis-(2-methoxyphenyl)-phosphino) napthalene sulfonic acid (~1.5 g) | Structure IV |
| 5 | benzene sulfonic acid (2.10 g) | 2-bromo-naphthalene (5.25 g) | 2-(bis-(2-naphthalenyl)-phosphino) benzene sulfonic acid (~2 g) | Structure V |
| 6 | benzene sulfonic acid (2.10 g) | Ferrocene (4.7 g) | 2-(bis(ferrocenyl)-phosphino) benzene sulfonic acid (~2 g) | Structure VI |

TABLE 1-continued

| Ex# | Component A | Component B | Product Solid/Yield | |
|---|---|---|---|---|
| | | | Chemical Name | Structure |
| 7 | benzene sulfonic acid (2.10 g) | Bromo-2,4,6-trimethoxybenzene (6.25 g) | 2-(bis(2,4,6-trimethoxybenzene-phenyl) phosphino) benzene sulfonic acid (~2 g) | Structure VII |
| 8 | benzene sulfonic acid (2.10 g) | Bromo-2,4,-dimethoxybenzene (5.5 g) | 2-(bis(2,4,-dimethoxy phenyl)-phosphino) benzene sulfonic acid (~2 g) | Structure VIII |
| 9 | benzene sulfonic acid (2.10 g) | Mesitylbromide (5.04 g) | 2-(bis(mesityl)-phosphino) benzene sulfonic acid (~2 g) | Structure IX |

TABLE 1-continued

| Ex# | Component A | Component B | Product Solid/Yield | |
|---|---|---|---|---|
| | | | Chemical Name | Structure |
| 10 | napthalenesulfonic acid (2.63 g) | Mesitylbromide (5.04 g) | 2-(bis(mesityl)-phosphino) napthalene sulfonic acid (~2.5 g) | Structure X |
| 11 | benzene sulfonic acid (2.10 g) | 2-bromobiphenyl (5.9 g) | 2-(bis-(2-biphenyl)-phosphino) benzene sulfonic acid (~2 g) | Structure XI |
| 12 | benzene sulfonic acid (2.10 g) | 3,5-di-t-butyl-bromobenzene (6.81 g) | 2-(bis-(3,5-di-t-butyl-phenyl) phosphino) benzene sulfonic acid (~2 g) | Structure XII |
| 13 | benzoic acid (2.10 g) | 2',6'dimethoxy-2-biphenylbromide (7.45 g) | 2-(bis-(2',6'dimethoxy-2-biphenyl) phosphino) benzoic acid (~5 g) | Structure XIII |

TABLE 1-continued

| Ex# | Component A | Component B | Chemical Name | Product Solid/Yield Structure |
|---|---|---|---|---|
| 14 | 4-nitrobenzene sulfonic acid (2.10 g) | 2-bromoanisole (4.75 g) | 2-(Bis(2-methoxy-phenyl)-phosphanyl)-4-nitro-benzenesulfonic acid (~2 g) | 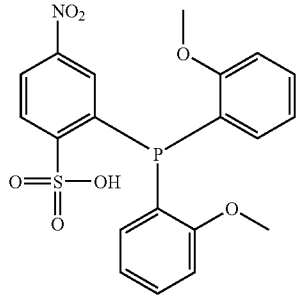<br>Structure XIV |
| 15 | benzene sulfonic acid (2.10 g) | Bromocyclohexane (4.13 g) | 2-Dicyclohexyl-phosphanyl-benzenesulfonic acid (~2 g) | 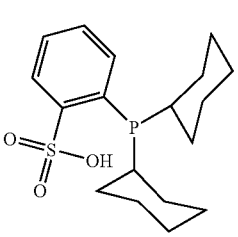<br>Structure XV |

EXAMPLE 16

Synthesis of a Potassium Salt of the Ligand of Structure VI

A 0.45 g (0.81 mmol) sample of Product Solid (i.e., ligand Structure VI) prepared according to Example 6 was added to 50 mL of THF in a reaction flask with vigorous agitation to form a ligand solution. In a separate container, 0.10 g (0.88 mmol) of potassium tert-butoxide was dissolved in 20 mL of THF. The resulting potassium tert-butoxide solution was then added dropwise to the contents of the reaction flask with agitation. Following the addition of the potassium tert-butoxide solution, the contents of the reaction flask were reduced by vacuum extraction of some of the THF solvent leaving approximately 25 mL of product solution in the reaction flask. A potassium salt of the ligand was then precipitated from the remaining product solution through the addition of 20 mL of pentane. The precipitated potassium salt of the ligand was recovered by filtration through a fine porosity frit and washed with pentane 3×20 mL. The potassium salt of the ligand was then subjected to vacuum to remove the remaining volatiles, leaving a dark orange Product Powder 0.40 g (0.67 mmol, 83%).

EXAMPLE 17

Synthesis of a Silver Salt of the Ligand of Structure VII

A 0.75 g (1.43 mmol) sample of the Product Solid (i.e., ligand Structure VII) prepared according to Example 7 was added to 50 mL of methanol in a reaction flask with vigorous agitation. In a separate container, 0.23 g (1.36 mmol) of silver nitrate was dissolved in 50 mL of deionized water. The resulting silver nitrate solution was then added dropwise to the contents of the reaction flask with vigorous agitation. Agitation of the contents of the reaction flask was continued for 20 minutes following addition of the silver nitrate solution. The contents of the reaction flask were then reduced by vacuum extraction of some of the solvent leaving approximately 50 mL and resulting in the formation of a gray precipitate. The precipitate was recovered by filtration through a fine porosity frit and washed with water 2×20 mL. The silver salt of the ligand was then dried under reduced pressure, leaving a dark gray Product Powder (0.35 g, 0.62 mmol, 44%).

EXAMPLES 18-31

Preparation Transition Metal Catalyst Complexes

A sample of Component A identified in Table 2 was added to 30 mL of tetrahydrofuran in a reaction flask with agitation. To the contents of the reaction flask was then added Component B identified in Table 2, with continued agitation. The contents of the reaction flask were then agitated for 30 minutes before adding Component C identified in Table 2. The contents of the reaction flask were then reduced under vacuum and pentane was added to precipitate the product catalyst complex. The product catalyst complex was collected by filtration through a fine porosity frit and washed with pentane 2×20 mL. The product catalyst complex was then subjected to vacuum to remove the remaining volatiles, leaving the Product Yield reported in Table 2.

TABLE 2

| Ex. # | Component A | Component B | Component C | Product Yield |
|---|---|---|---|---|
| 18 | Product Solid prepared according to Example 1 (0.943 g) | dimethyl tetramethyl-ethylene diamine palladium (II) (0.388 g) | Pyridine (~0.2 ml) | 940 mg |
| 19 | Product Solid prepared according to Example 2 (340 mg) | dimethyl tetramethyl-ethylene diamine palladium (II) (200 mg) | Pyridine (~0.2 ml) | 440 mg |
| 20 | Product Solid prepared according to Example 3 (79 mg) | dimethyl tetramethyl-ethylene diamine palladium (II) (50 mg) | Pyridine (~0.2 ml) | 87 mg |
| 21 | Product Solid prepared according to Example 4 (45 mg) | dimethyl tetramethyl-ethylene diamine palladium (II) (25 mg) | Pyridine (~0.2 ml) | 33 mg |
| 22 | Product Solid prepared according to Example 5 (44 mg) | dimethyl tetramethyl-ethylene diamine palladium (II) (25 mg) | Pyridine (~0.2 ml) | 41 mg |
| 23 | Product Solid prepared according to Example 8 (0.370 g) | dimethyl tetramethyl-ethylene diamine palladium (II) (0.200 g) | Pyridine (~0.2 ml) | 440 mg |
| 24 | Product Solid prepared according to Example 9 (0.640 g) | dimethyl tetramethyl-ethylene diamine palladium (II) (0.350 g) | Pyridine (~0.2 ml) | 700 mg |
| 25 | Product Solid prepared according to Example 11 (0.396 g) | dimethyl tetramethyl-ethylene diamine palladium (II) (0.200 g) | Pyridine (~0.2 ml) | 540 mg |
| 26 | Product Solid prepared according to Example 12 (0.2272 g) | dimethyl tetramethyl-ethylene diamine palladium (II) (0.100 g) | Pyridine (~0.2 ml) | 320 mg |
| 27 | Product Solid prepared according to Example 13 (210 mg) | dimethyl tetramethyl-ethylene diamine palladium (II) (150 mg) | Pyridine (~0.2 ml) | 200 mg |
| 28 | Product Solid prepared according to Example 14 (115 mg) | dimethyl tetramethyl-ethylene diamine palladium (II) (50 mg) | Pyridine (~0.2 ml) | 78 mg |
| 29 | Product Solid prepared according to Example 15 (83 mg) | dimethyl tetramethyl-ethylene diamine palladium (II) (50 mg) | Pyridine (~0.2 ml) | 5 mg |
| 30 | Product Powder prepared according to Example 16 (0.135 g) | (1,5 cyclooctadiene) methyl palladium (II) triflate (0.086 g) | none | 148 mg |
| 31 | Product Powder prepared according to Example 17 (0.098 g) | chloro(1,5 cyclooctadiene) methyl palladium (II) (0.046 g) | none | 780 mg |

EXAMPLE 32

Preparation of Transition Metal Catalyst Complex & Heck Coupling

A reaction flask was charged with 0.02 g (30 µmol) of palladium acetate and 0.025 g (70 µmol) of a Product Solid (i.e., ligand Structure XIII) prepared according to Example 13. The contents were dissolved in 1.5 mL of benzene. Bromobenzene (50 µL, 0.21 mmol) and methylacrylate (50 µL, 0.58 mmol) were added to the reaction flask followed by the addition of excess sodium acetate. The reaction was heated for 24 hours. Based on limiting reagent, conversion to 3-Phenyl-acrylic acid methyl ester was determined to be 30%.

EXAMPLE 33

Catalyst Preparation/Polymerization

An 8 mL serum vial equipped with a stirring bar in a glovebox was charged with palladium bis(dibenzylideneacetone) (41.1 mg, 72.0 µmol); product solid (i.e., ligand Structure IX) prepared according to Example 9 (45.0 mg, 86.4 µmol) and toluene (4.5 mL). The contents of the serum vial were allowed to stir for 10 minutes, producing a red/brown mixture (i.e., catalyst complex).

A reactor cell in a glovebox was charged with methyl acrylate (1.0 mL, 11.1 mmol), followed by the addition of toluene (4.0 mL). The reactor was then heated to 100° C. with agitation. The reactor cell was then pressurized with ethylene gas to 400 psig. After equilibration, a sample of catalyst complex as described above (0.5 mL, 8 µmol Pd) was injected into the reactor cell, followed by a 0.5 mL toluene rinse. After 60 minutes, the reactor cell was vented and allowed to cool. The reactor cell was then removed from the glovebox. The reactor cell was observed to contain a green colored liquid with a black precipitate. The black precipitate dissolved when added to acidified MeOH (10% HCl). No polymer was observed to form.

EXAMPLE 34

Catalyst Preparation/Polymerization

A sample of Product Solid (i.e., ligand Structure IX) prepared according to Example 9 (0.640 g, 1.40 mmol) was added to 30 mL of THF in a reaction flask with agitation. Dimethyl tetramethylethylenediamine palladium (II) (0.350 g, 1.40 mmol) was then added to the reaction flask with agitation. The contents of the reaction flask were agitated for 30 minutes before adding dry pyridine (0.185 mL, 2.1 mmol). The contents of the reaction flask were then reduced under vacuum and pentane was added to precipitate the catalyst complex. The catalyst complex was collected by filtration through a fine porosity frit and washed with pentane 2×20 mL. The catalyst complex was then subjected to vacuum to remove the remaining volatiles, leaving a white solid (0.68 g, 1.09 mmol, 78%).

Methyl acrylate (1.0 mL, 11.1 mmol), followed by toluene (4.0 mL), were charged to a reactor cell in a glovebox. The contents of the cell were then heated to 80° C. and pressurized with ethylene gas to 400 psig. After equilibration, a sample of the catalyst complex prepared above (3 mg, 4.8 µmol) was dissolved in 0.5 mL toluene and was injected into the reactor cell, followed by a 0.5 mL toluene rinse. After 60 minutes, the reactor cell was vented and allowed to cool. The contents of the reactor cell were then removed from the glovebox and were added to rapidly stirred MeOH. After 60 minutes, the resulting mixture was filtered on a glass frit, washed with excess MeOH and dried overnight at 60° C. under vacuum. The subject reaction yielded 0.10 g of a random copolymer of ethylene and methyl acrylate.

EXAMPLE 35-42

Polymerization

A reactor cell in a glovebox was charged with the Monomer Component identified in Table 3, followed by THF (4.0 mL). The contents of the reactor cell were then heated to 80° C. and pressurized with ethylene gas to 400 psig. After equilibration, 0.5 mL of tetrahydrofuran containing the Catalyst Component identified in Table 3 was injected into the reactor cell, followed by a tetrahydrofuran rinse (0.5 mL). After 60 minutes, the reactor cell was vented and allowed to cool. The contents of the reactor cell were then removed from the glovebox and added to rapidly stirred MeOH. After stirring for 60 minutes, the polymer was vacuum filtered and dried under vacuum at 60° C. for 18 hours. The Product Yield of random copolymer obtained from the reaction was as reported in Table 3.

TABLE 3

| Ex. # | Monomer Component | Catalyst Component | Random Copolymer Product Yield |
|---|---|---|---|
| 35 | butyl acrylate (1.0 mL, 6.98 mmol) | Product of Ex # 19 (4.2 μmol Pd) | 0.28 g |
| 36 | butyl acrylate (1.0 mL, 6.98 mmol) | Product of Ex #26 (0.5 mL, 8.0 μmol Pd) | 0.1 g |
| 37 | butyl acrylate (1.0 mL, 6.98 mmol) | Product of Ex #30 (0.5 mL, 8.0 μmol Pd) | 0.1 g |
| 38 | styrene (1.0 mL, 8.73 mmol) | Product of Ex #26 (0.5 mL, 8.0 μmol Pd) | 0.21 g |
| 39 | styrene (1.0 mL, 8.73 mmol) | Product of Ex #30 (0.5 mL, 8.0 μmol Pd) | 0.10 g |
| 40 | styrene (1.0 mL, 8.73 mmol) | Product of Ex #25 (0.5 mL, 8.0 μmol Pd) | 0.58 g |
| 41 | isobornyl acrylate (1.0 mL, 4.73 mmol) | Product of Ex #19 (0.5 mL, 4.2 μmol Pd) | 0.44 g |
| 42 | isobornyl acrylate (1.0 mL, 4.73 mmol) | Product of Ex #26 (0.5 mL, 8.0 μmol Pd) | 0.15 g |

EXAMPLE 43

Polymerization

To an 8 mL serum vial equipped with a stirring bar in a glovebox was added palladium bis(dibenzylideneacetone) (41.1 mg, 72.0 μmol); a sample of the Product Solid (i.e., ligand Structure XII) prepared according to Example 12 (45.0 mg, 86.4 μmol) and toluene (4.5 mL). The contents of the serum vial were allowed to stir for 10 minutes, producing a red/brown mixture (i.e., catalyst complex).

Three separate reactor cells in a glovebox were each charged with butyl acrylate (1.0 mL, 11.1 mmol), followed by toluene (4.0 mL). The contents of the separate reactor cells were then pressurized with ethylene gas to 400 psig and heated to the temperature noted in Table 4. After equilibration, a 0.5 mL sample of the catalyst complex prepared above (8.0 μmol Pd) was injected into each reactor cell, followed by a toluene rinse (0.5 mL). After 60 minutes, the reactor cells were vented and allowed to cool. The contents of the reactor cells were then removed from the glovebox and separately added to rapidly stirred MeOH. After stirring for 60 minutes, the product polymer in each reactor cell was separately vacuum filtered and dried under vacuum at 60° C. for 18 hours. The polymer yield, butyl acrylate incorporation, weight average molecular weight, $M_w$, number average molecular weight, $M_n$ and PDI (i.e., $M_w/M_n$) for each reactor cell are reported in Table 4.

TABLE 4

| Reactor Cell # | Reaction Temp | Polymer Yield | Butyl acrylate incorporation | Mw (g/mol) | Mn (g/mol) | PDI |
|---|---|---|---|---|---|---|
| 1 | 90° C. | 0.65 g | 1.1 mol % | 108,000 | 72,000 | 1.5 |
| 2 | 110° C. | 0.48 g | 1.2 mol % | 68,000 | 40,000 | 1.7 |
| 3 | 120° C. | 0.30 g | 1.7 mol % | 43,000 | 25,000 | 1.7 |

EXAMPLE 44

Polymerization

Styrene (1.0 mL, 8.73 mmol) and norbornene (1.0 mL, 7.98 mmol, 85 mol % norbornene in toluene) were charged to a reactor cell in a glovebox. Toluene (4.0 mL) was then charged to the reactor cell. The contents of the reactor cell were then heated to 80° C. and pressurized with ethylene gas to 400 psig. After equilibration, a sample of a catalyst complex prepared according to Example 18 (1.6 mg, 2 μmol) was dissolved in 0.5 mL toluene and was injected into the reactor cell, followed by a 0.5 mL toluene rinse. After 60 minutes, the reactor cell was vented and allowed to cool. The contents of the reactor cell were then removed from the glovebox and were added to rapidly stirred MeOH. After 60 minutes, the resulting mixture was filtered on a glass frit, washed with excess MeOH and dried overnight at 60° C. under vacuum. The subject reaction yielded 0.20 g of a random copolymer of ethylene, styrene and norbornene.

EXAMPLE 45

Polymerization

Methyl acrylate (1.0 mL, 11.1 mmol) and norbornene (1.0 mL, 7.98 mmol, 85 mol % norbornene in toluene) were charged to a reactor cell in a glovebox. Toluene (4.0 mL) was then charged to the reactor cell. The contents of the reactor cell were then heated to 80° C. and pressurized with ethylene gas to 400 psig. After equilibration, a sample of a catalyst complex prepared according to Example 18 (1.6 mg, 2 μmol) was dissolved in 0.5 mL toluene and was injected into the reactor cell, followed by a 0.5 mL toluene rinse. After 60 minutes, the reactor cell was vented and allowed to cool. The contents of the reactor cell were then removed from the glovebox and were added to rapidly stirred MeOH. After 60 minutes, the resulting mixture was filtered on a glass frit, washed with excess MeOH and dried overnight at 60° C. under vacuum. The subject reaction yielded 0.59 g of a random copolymer of ethylene, methyl acrylate and norbornene.

EXAMPLE 46

Polymerization

Methyl acrylate (1.0 mL, 11.1 mmol) and styrene (1.0 mL, 8.73 mmol) were charged to a reactor cell in a glovebox. Toluene (4.0 mL) was then charged to the reactor cell. The contents of the reactor cell were then heated to 80° C. and pressurized with ethylene gas to 400 psig. After equilibration, a sample of a catalyst complex prepared according to Example 18 (1.6 mg, 2 μmol) was dissolved in 0.5 mL toluene and was injected into the reactor cell, followed by a 0.5 mL toluene rinse. After 60 minutes, the reactor cell was vented and allowed to cool. The contents of the reactor cell were then removed from the glovebox and were added to rapidly stirred MeOH. After 60 minutes, the resulting mixture was filtered on a glass frit, washed with excess MeOH and dried overnight at 60° C. under vacuum. The subject reaction yielded 0.81 g of a random copolymer of ethylene, methyl acrylate and styrene.

EXAMPLE 47

Polymerization

To a 5 mL serum vial was added 41.4 mg (72 µmol) Palladium bis(dibenzylideneacetone) and 53.1 mg (86.4 µmol) of a Product Solid (i.e., ligand Structure I) prepared according to Example 1. To this vial was then added 4.5 ml THF. The contents of the serum vial were stirred for several minutes to prepare a catalyst complex.

Methyl acrylate (1.0 mL, 11.1 mmol) and THF (4.0 mL), were charged to a reactor cell in a glovebox. The contents of the reactor cell were then heated to 70° C. and pressurized with ethylene gas to 400 psig. After equilabration, 0.1 mL (1.6 µmol) of the catalyst complex from the serum vial was injected into the reactor cell, followed by a 0.5 mL THF rinse. After 60 minutes, the reactor cell was vented and allowed to cool. The contents of the reactor cell were then removed from the glovebox and were added to rapidly stirred MeOH. After 60 minutes, the resulting mixture was filtered on a glass frit, washed with excess MeOH and dried overnight at 60° C. under vacuum. The subject reaction yielded 1.02 g of a random copolymer of ethylene and methyl acrylate with an acrylate incorporation of 4.8 mol %; a weight average molecular weight, $M_w$, of 474,000 and a number average molecular weight, $M_n$, of 178,000.

EXAMPLE 48

Polymerization

To a 5 mL serum vial was added 41.4 mg (72 µmol) Palladium bis(dibenzylideneacetone) and 53.1 mg (86.4 µmol) of a Product Solid (i.e., ligand Structure I) prepared according to Example 1. To this vial was then added 4.5 ml THF. The contents of the serum vial were stirred for several minutes to prepare a catalyst complex.

Methyl acrylate (1.0 mL, 11.1 mmol) and THF (4.0 mL), were charged to a reactor cell in a glovebox. The contents of the reactor cell were then heated to 70° C. and pressurized with ethylene gas to 400 psig. After equilabration, 0.1 mL (8.0 µmol) of the catalyst complex from the serum vial was injected into the reactor cell, followed by a 0.5 mL THF rinse. After 60 minutes, the reactor cell was vented and allowed to cool. The contents of the reactor cell were then removed from the glovebox and were added to rapidly stirred MeOH. After 60 minutes, the resulting mixture was filtered on a glass frit, washed with excess MeOH and dried overnight at 60° C. under vacuum. The subject reaction yielded 1.28 g of a random copolymer of ethylene and methyl acrylate with an acrylate incorporation of 2.7 mol % and a weight average molecular weight, $M_w$, of 172,000 and a number average molecular weight, $M_n$, of 57,000.

EXAMPLE 49

Polymerization

To a 5 mL serum vial was added 41.4 mg (72 µmol) Palladium bis(dibenzylideneacetone) and 53.1 mg (86.4 µmol) of a Product Solid (i.e., ligand Structure I) prepared according to Example 1. To this vial was then added 4.5 ml toluene. The contents of the serum vial were stirred for several minutes to prepare a catalyst complex.

Methyl acrylate (1.0 mL, 11.1 mmol) and toluene (4.0 mL), were charged to a reactor cell in a glovebox. The contents of the reactor cell were then heated to 50° C. and pressurized with ethylene gas to 400 psig. After equilabration, 0.5 mL (8.0 µmol) of the catalyst complex from the serum vial was injected into the reactor cell, followed by a 0.5 mL toluene rinse. After 60 minutes, the reactor cell was vented and allowed to cool. The contents of the reactor cell were then removed from the glovebox and were added to rapidly stirred MeOH. After 60 minutes, the resulting mixture was filtered on a glass frit, washed with excess MeOH and dried overnight at 60° C. under vacuum. The subject reaction yielded 0.81 g of a random copolymer of ethylene and methyl acrylate with an acrylate incorporation of 0.4 mol %; a weight average molecular weight, $M_w$, of 716,000 and a number average molecular weight, $M_n$, of 388,000.

EXAMPLE 50

Ligand Synthesis

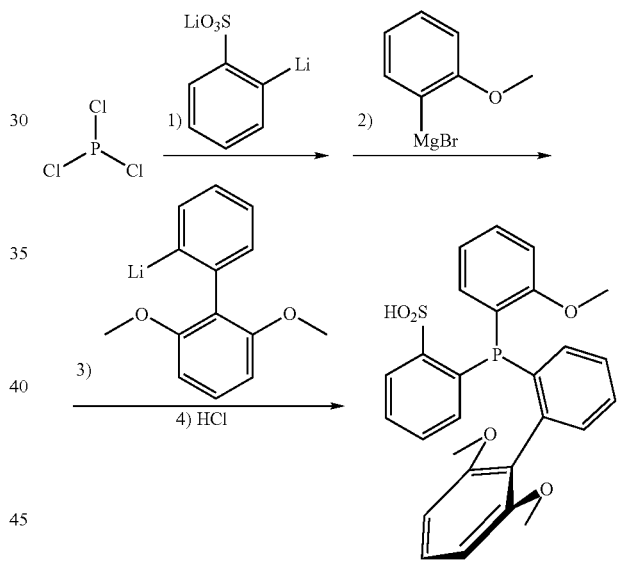

A first 100 mL Schlenk flask was charged with benzenesulfonic acid hydrate (1.7 g, 10.7 mmol, $C_6H_6O_3S.H_2O$, 158.71 g/mol, MP Bio Medicals 98-11-3). The flask was evacuated under vacuum. The bottom of the flask was then heated using a heat gun. The flask contents melted to form a brown liquid, which started bubbling. The heating was continued until the liquid started to reflux and the pressure dropped to approximately 10 mTorr. The flask was filled with nitrogen, cooled and THF (anhydrous, Acros, ~50 mL) was added to the flask forming a clear colorless solution. At 0° C., n-BuLi (2.5 M hexane solution, 11.4 mmol, 8.6 mL, Aldrich) was added to yield a beige suspension, which was stirred for 0.5 hr before being cooled at −78° C.

A second 100 mL Schlenk flask was charged with Mg (0.30 g, 0.0125 mmol, powder, Aldrich). THF (50 mL, anhydrous, Acros) and 2-bromoanisole (2.10 g, 0.0112 mmol, $C_7H_7BrO$, 187.04 g/mol, Acros) were added to the second Schlenk flask. The contents of the second Schlenk flask were sonicated (~30 sec.) and the contents were observed to exhibit a temperature rise. The mixture was stirred until it cooled back down to room temperature.

A 200 mL Schlenk flask was charged with THF (~50 mL). At −78° C., PCl$_3$ (0.93 mL, 1.47 g, 0.0107 mol, 1.574 g/mL, 137.33 g/mol, Aldrich) was added to the 200 mL Schlenk flask via syringe. The beige suspension in the first 100 mL Schlenk flask was transferred to the 200 mL Schlenk flask at −78° C. via cannula. The contents of the 200 mL Schlenk flask were then stirred for 0.5 hours while maintaining the temperature at −78° C. The contents of the second 100 mL Schlenk flask was cooled to −78° C. and transferred to the 200 mL Schlenk flask via cannula. The contents of the 200 mL Schlenk flask were then warmed to ambient temperature and stirred for about an hour to yield a yellow solution.

A 500 mL Schlenk flask was charged with 2'-Br-2,6-(Me)$_2$ biphenyl (3.14 g, 10.7 mmol, $C_{14}H_{13}BrO_2$, 293.16 g/mol, Aldrich) ant THF (150 mL). The contents of the 500 mL Schlenk flask were cooled to −78° C. n-BuLi (4.3 mL, 2.5 M hexane solution, 10.7 mmol, Aldrich) at −78° C. was added to the 500 mL Schlenk flask, yielding a thick, white slurry. The 500 mL Schlenk flask was shaken by hand to ensure mixing. A 0.5 hour after the addition of the n-BuLi, the contents of the 200 mL Schlenk flask were added to the 500 mL Schlenk flask via cannula. The contents of the 500 mL Schlenk flask were then allowed to gradually warm to ambient temperature. The contents of the 500 mL Schlenk flask were stirred overnight to yield a clear yellow solution. The volatiles were removed from the 500 mL Schlenk flask under vacuum. The resulting solid was extracted using CH$_2$Cl$_2$ (200 mL), H$_2$O (200 mL), HCl (concentrated, 20 mL). The organic layer from the extract was dried with MgSO$_4$ and the volatile portion of the extract was removed under vacuum to leave a pale yellow solid. The pale yellow solid was collected and washed with THF (3×15 mL) and Et$_2$O (3×15 mL) to yield a white powder product ligand (2.3 g, 44% yield). $^1$H NMR (CDCl$_3$, ° C.): δ8.32 (m, 1H), 7.71 (q, J=8.5, 2H), 7.56 (m, 1H), 7.47-7.40 (m, 4H), 7.33-7.27 (m, 2H), 6.99 (m, 2H), 6.91 (m, 1H), 6.57 (d, J=8.5, 1H), 6.44 (d, J=8.5, 1H), 3.73 (s, 3H), 3.64 (s, 3H), 3.19 (s, 3H). $^{31}$P NMR (CDCl$_3$, ° C.): δ−7.1 (s). LC-MS: m/z=509.2.

EXAMPLE 51

Polymerization

The vial was charged with Pd(dba)$_2$ (19.8 mg, 0.0340 mmol, Pd(C$_{17}$H$_{14}$O)$_2$, Alfa Aesar, 575.00 g/mol) and the product ligand of Example 50 (20.0 mg, 0.0390 mmol, C$_{27}$H$_{25}$O$_6$PS, 508.53 g/mol). Toluene (10 mL) was then added to the vial. The contents of the vial were vigorously shaken to yield a dark red catalyst solution with a trace amount of particles.

A reactor cell was charged with methyl acrylate (1 mL) and toluene (4 mL). The reactor cell was heated to 90° C. Ethylene was then charged to the reactor cell (400 psi). The catalyst solution (0.5 mL) from the vial was added to the reactor cell vial cannula followed by a toluene rinse (0.5 mL). The reactor cell contents were stirred at 90° C. for 1 hour. The unreacted ethylene was vented from the reactor cell and the contents of the reactor cell were cooled to ambient temperature. The contents of the reactor cell were then quenched with methanol (100 mL). The precipitated polymer in the reactor cell was separated by centrifuge and dried under vacuum at 60° C. overnight to yield a white solid (720 mg). $^1$H NMR spectroscopy revealed that the white solid had a composition of ethylene (97 mole %) and methyl acrylate (3 mole %). GPC analysis revealed that the white solid had a weight average molecular weight of 115,000 g-mol$^{-1}$ with a polydispersity of 1.5.

We claim:

1. A process for making a ligand having the formula

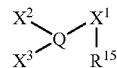

wherein the process comprises the following reactions:

(a) $X^1(R^{15})$—$E^1$ + $V^1$—$Q(V^3)V^2$ → $X^1(R^{15})$—$Q(V^3)V^2$ (Compound I)

(b) $X^2$—$E^2$ + $X^1(R^{15})$—$Q(V^3)V^2$ (Compound I) → $X^1(R^{15})$—$Q(V^3)$—$X^2$ (Compound II)

(c) $X^3$—$E^3$ + $X^1(R^{15})$—$Q(V^3)$—$X^2$ (Compound II) → $X^1(R^{15})$—$Q(X^3)$—$X^2$ (Compound III);

wherein Q is selected from phosphorus, arsenic and antimony;

wherein $E^1$, $E^2$ and $E^3$ are electrophilic metals;

wherein $V^1$, $V^2$ and $V^3$ are weakly-basic anions;

wherein $X^1$, $X^2$ and $X^3$ are carbon anions; and, wherein $R^{15}$ is selected from —SO$_3$H, —SO$_2$N(R$^{18}$), —CO$_2$H, —PO$_3$H, —AsO$_3$H, —SiO$_2$H, —C(CF$_3$)$_2$O; where $R^{18}$ is selected from a hydrogen, a halogen, a hydrocarbyl group and a substituted hydrocarbyl group.

2. The process of claim 1, wherein $X^1(R^{15})$—$E^1$, $X^2$—$E^2$ and $X^3$—$E^3$ are according to formulas I, II, and III, respectively,

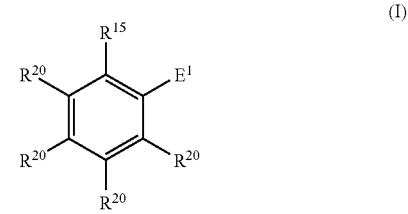

(I)

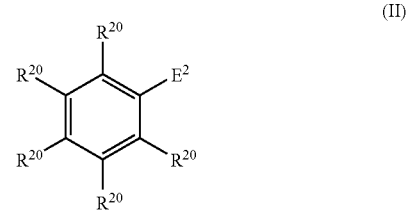

(II)

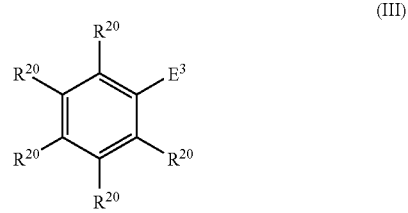

(III)

wherein $E^1$, $E^2$ and $E^3$ are electrophilic metals;

wherein $R^{15}$ is selected from —SO$_3$, —SO$_2$N(R$^{18}$), —CO$_2$, —PO$_3$, —AsO$_3$, —SiO$_2$, —C(CF$_3$)$_2$O; where $R^{18}$ is selected from a hydrogen, a halogen, a hydrocarbyl group and a substituted hydrocarbyl group; and, wherein each $R^{20}$ is independently selected from a hydrogen; a halogen; and, a substituted or unsubstituted substituent selected from $C_1$-$C_{20}$ alkyl, $C_3$-$C_{20}$ cycloalkyl, $C_2$-$C_{20}$ alkenyl, $C_2$-$C_{20}$ alkynyl, aryl, arylalkyl, alkylaryl, phenyl, biphenyl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl, $C_1$-$C_{20}$ alkylsulfinyl, and silyl.

3. The process of claim 1, wherein reactions (a), (b) and (c) are done sequentially in the same vessel, wherein the reaction temperature during reaction (a) is less than the reaction temperature during reaction (b) and wherein the reaction temperature during reaction (b) is less than the reaction temperature during reaction (c).

4. The process of claim 1, wherein reaction (b) proceeds in the same vessel as reaction (a) without isolation of Compound I.

5. The process of claim 4, wherein reaction (c) proceeds in the same vessel as reaction (a) and reaction (b) without isolation of Compound II.

6. The process of claim 1, wherein no protecting groups are used.

7. A process for making a ligand having the formula

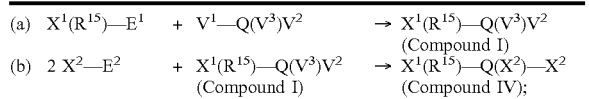

wherein the process comprises the following reactions:

| (a) | $X^1(R^{15})$—$E^1$ | + | $V^1$—$Q(V^3)V^2$ | → | $X^1(R^{15})$—$Q(V^3)V^2$ (Compound I) |
| (b) | $2\ X^2$—$E^2$ | + | $X^1(R^{15})$—$Q(V^3)V^2$ (Compound I) | → | $X^1(R^{15})$—$Q(X^2)$—$X^2$ (Compound IV); | wherein Q is selected from phosphorus, arsenic and antimony;
wherein $E^1$ and $E^2$ are electrophilic metals;
wherein $V^1$, $V^2$ and $V^3$ are weakly-basic anions;
wherein $X^1$ and $X^2$ are carbon anions; and,
wherein $R^{15}$ is selected from —$SO_3H$, —$SO_2N(R^{18})$, —$CO_2H$, —$PO_3H$, —$AsO_3H$, —$SiO_2H$, —$C(CF_3)_2O$; where $R^{18}$ is selected from a hydrogen, a halogen, a hydrocarbyl group and a substituted hydrocarbyl group.

* * * * *